United States Patent
Amir et al.

(10) Patent No.: US 6,340,458 B1
(45) Date of Patent: Jan. 22, 2002

(54) USE OF ENZYMES FOR SKIN EXPANSION

(76) Inventors: Reva Amir; Abraham Amir, both of 2 Hashikma Street, Tel Mond 40600 (IL)

( * ) Notice: Subject to any disclaimer, the term of this patent is extended or adjusted under 35 U.S.C. 154(b) by 0 days.

(21) Appl. No.: 09/443,381

(22) Filed: Nov. 19, 1999

(51) Int. Cl.$^7$ ............................................... A61K 38/48
(52) U.S. Cl. .................................................... 424/94.64
(58) Field of Search ....................................... 424/94.64

(56) References Cited

U.S. PATENT DOCUMENTS

| | | | |
|---|---|---|---|
| 3,864,477 A | * 2/1975 | Thuillier et al. | 424/94.64 |
| 4,276,281 A | 6/1981 | Crikelair | 424/84 |
| 4,645,668 A | 2/1987 | Pinnell | 424/94 |
| 5,508,195 A | * 4/1996 | Christner et al. | 435/265 |

FOREIGN PATENT DOCUMENTS

JP     04124141 A2 * 4/1992

OTHER PUBLICATIONS

Bouloc et al., Dermatology 198:346–350 (1999).*
Hwang et al., Arch. Dermatol. 131: 1175–1177 (Oct. 1995).*
Robert, L., Interaction elastin and elasteses and its role in the aging of the arterial wall, skin, and other connective tissues. A Review. Mechanisms of Ageing and Development. 1984, vol. 28, pp. 155–166.
Raub et al. Dose Response of Elastase–Induced Emphysema in Hamsters. American Review of Respiratory Diseases. 1982, vol. 125, pp. 432–435.

* cited by examiner

*Primary Examiner*—Jean C. Witz
(74) *Attorney, Agent, or Firm*—Pillsbury Winthrop LLP

(57) ABSTRACT

There is disclosed a method for expanding healthy skin, comprising administering to healthy skin an efficacious amount of an enzyme which cleaves elastin fibers, preferably elastase or an elastase derivative. The method may be used in the treatment of skin diseases or disorders occuring in areas adjacent to the healthy skin, including treatment of skin loss after excision of a skin tumor or excision of necrotic skin, trauma, a congenital skin condition, and a condition which has resulted or is likely to result in skin loss. There is also disclosed a method for increasing the yield of leather from an animal, comprising contacting the hide of said animal, or a portion of said hide, with an efficacious amount of an enzyme which cleaves elastin fibers, preferably elastase or an elastase derivative.

26 Claims, No Drawings

USE OF ENZYMES FOR SKIN EXPANSION

FIELD OF THE INVENTION

The present invention relates to methods for treating human and animal skins to expand said skins.

BACKGROUND OF THE INVENTION

The skin is composed of an epidermis and a dermis. The dermis is composed collagen and elastin fibers as well as other components. The elastin fibers act like springs, and thus impart to skin its elastic recoil. Broken or destroyed elastin fibers can be found in the following conditions:

(a) The aging process: the skin of aged people is wrinkled because of the high percentage of broken elastin fibers, which prevents the skin from retaining its tautness.

(b) Cutis Laxa disease: this is a genetic disease in which elastin fibers are destroyed during adolescence, causing the skin of teenagers to wrinkle and giving them the appearance of old age.

U.S. Pat. No. 4,645,668 describes a method for the prevention and treatment of scars by repeatedly injecting collagenase into various types of disfiguring lesions (keloid, hypertrophic scars, disfiguring surgical scars, acne scars, and fibrotic bands). Therapy was discontinued when the scar appearance was satisfactory.

U.S. Pat. No. 4,276,281 describes the use of elastase in the form of an ointment to promote the healing of skin burns in rats. Application of the ointment hastened the removal of the burn eschar.

The disclosures of all references mentioned above and throughout the present specification are hereby incorporated herein by reference.

SUMMARY OF THE INVENTION

The present invention seeks to provide an improved method for expanding skin.

There is thus provided in accordance with a preferred embodiment of the present invention a method for expanding healthy skin, comprising administering to healthy skin an efficacious amount of an enzyme which cleaves elastin fibers. In a preferred embodiment of the invention, the enzyme is elastase or an elastase derivative.

In one preferred embodiment of the invention, the enzyme is administered by injection. In another preferred embodiment of the invention, the enzyme is administered by topical application. Preferably, the enzyme is administered in an concentration selected from (a) a concentration of at least 1 unit of activity per $cm^2$ of skin or (b) a concentration of at least 1 mg of enzyme per $cm^2$ of skin.

In a preferred embodiment of the invention, the healthy skin is adjacent to an area of skin which suffers from a condition or deficiency. In on preferred embodiment, the condition or deficiency is selected from the group consisting of: (a) skin loss after excision of a skin tumor or excision of necrotic skin; (b) trauma; (c) a congenital condition; and (d) a condition which has resulted or is likely to result in skin loss.

In another preferred embodiment of the present invention, the healthy skin is adjacent to an area of skin which is to undergo reconstructive surgery.

There is also provided, in accordance with a preferred embodiment of the invention, a method for increasing the surface area of a piece of skin to be applied as a skin graft, comprising contacting the piece of skin with an efficacious amount of an enzyme which cleaves elastin fibers. In a preferred embodiment of the invention, the enzyme is elastase or an elastase derivative.

In one preferred embodiment of the invention, the piece of skin is contacted with the enzyme by injecting the enzyme into the piece of skin. In another preferred embodiment of the invention, the piece of skin is contacted with the enzyme by topically applying the enzyme to the piece of skin. In yet another preferred embodiment of the invention, the piece of skin is contacted with the enzyme by soaking the piece of skin in a solution containing the enzyme.

There is also provided, in accordance with a preferred embodiment of the invention, a method for increasing the yield of leather from an animal, comprising contacting the hide of the animal or a portion thereof with an efficacious amount of an enzyme which cleaves elastin fibers. In a preferred embodiment of the invention, the enzyme is elastase or an elastase derivative.

In one preferred embodiment of the invention, the hide or portion thereof is on a live animal. In another preferred embodiment of the invention, the hide or portion thereof has been removed from the animal but has not yet been cured or tanned.

In one preferred embodiment of the invention, the hide or portion thereof is contacted with the enzyme by injecting the enzyme into the hide or portion thereof. In another preferred embodiment of the invention, the hide or portion thereof is contacted with the enzyme by topically applying the enzyme to the hide or portion thereof. In yet another preferred embodiment of the invention, the hide or portion thereof is contacted with the enzyme by soaking the hide or portion thereof in a solution containing the enzyme.

There is also provided, in accordance with a preferred embodiment of the invention, an animal hide or portion thereof which has been expanded by contacting said hide or portion thereof with an efficacious amount of an enzyme which cleaves elastin fibers.

There is also provided, in accordance with a preferred embodiment of the invention, a method for imitating in a person with healthy skin the pathological condition of the skin of a person suffering from Cutis Laxa disease, comprising administering to a region of healthy skin of said person in which region it is desired to imitate said pathological condition an efficacious amount of an enzyme which cleaves elastin fibers.

There is also provided, in accordance with a preferred embodiment of the invention, a method for decreasing the elastic resistance of skin to pulling, comprising administering to said skin an efficacious amount of an enzyme which cleaves elastin fibers.

DETAILED DESCRIPTION OF A PREFERRED EMBODIMENT

Without wishing to be bound by any particular theory, it is believed that the present invention is based on the ability of certain enzymes, particularly elastase or elastase derivatives, to cleave the elastin fibers in the skin of humans and other animals. It is believed that contacting such skin with such an enzyme results in the loss of the elastic recoil of the skin so contacted, "loosening" the skin and causing its expansion. Such contacting can be effected by any suitable means, including by injection, by topical administration, and in cases of skin which has been removed from the person or animal on which it grew, by soaking in an enzyme-containing solution.

Throughout this description and the claims that follow, the term "elastase or elastase derivatives" will be understood to refer to elastase from various animal sources, as well as elastases which have been modified by genetic engineering to contain point mutations, amino acid insertions or deletions, as well as elastases which have been conjugated, bonded, coupled or otherwise linked to other molecules, or which have been chemically modified, but which still substantially maintain their enzymic activity. The term "healthy skin" will be understood to mean skin which is relatively healthy for a patient or animal of that age.

Skin expanded by the method of the present invention has uses in several areas:

Surgery: The enzyme, e.g. elastase, can be injected or be applied topically to healthy skin, particularly in proximity to areas of skin loss, before, during or after surgery. Such areas of skin loss can be seen after excision of skin tumors or necrotic skin (e.g. from burns or wounds), after trauma, as a result of congenital conditions such as aplasia cutis congenita, after mastectomy, and in other skin deficiency conditions. The expanded healthy skin can be used to help cover the area of skin loss, e.g. in breast reconstruction.

Skin grafts: Applying the enzyme to pieces of skin to be used for skin grafts, or contacting said pieces with the enzyme by soaking or topical application, either during or after surgery or while the skin to be grafted is in a skin bank, can increase the amount of skin surface available for grafting.

Leather industry: contacting animal hides or portions thereof with enzyme, either while the animal is alive or after the hide has been removed from the carcass but before curing or tanning, can increase the yield of leather from a single animal.

Although the ability of elastase to cleave elastin is well-known in the art, prior to the present invention it was not known to utilize elastase to expand healthy human skin, whether of live patients or in a skin bank, nor was it known to utilize elastase or other enzymes to expand the skin available from animals whereby to increase the yield of leather from an animal.

The invention will be better understood from the following detailed description of a preferred embodiment thereof. Ten fresh samples of healthy skin 5.5 cm in length and 0.6 cm in width which had been removed from the legs of patients were incubated in Tris HCl buffer (Sigma Product No. T-1503) at pH 8.8 and 37° C. for 24 hours.

Five of the skin samples were designated control samples and five were designated test samples. Immediately prior to incubation, each control sample was intradermally injected with 2.5 ml of the aforementioned Tris HCl buffer. Immediately prior to incubation, each test sample was injected with 2.5 ml of this same buffer, but which contained in addition 3.5 mg of elastase (porcine pancreas elastase, Sigma product no. E6883, 1–3 units of activity per mg) diluted therein.

Following the 24-hour incubation, one end of each sample was fixed with a nail and the other end of each sample was weighted with a 10 g weight. The length of each sample was measured, and the following results were obtained:

|  | Control Samples | | | | | Test Samples | | | | |
| --- | --- | --- | --- | --- | --- | --- | --- | --- | --- | --- |
| Sample No. | 1 | 2 | 3 | 4 | 5 | 6 | 7 | 8 | 9 | 10 |
| Length after incubation (cm) | 5.6 | 5.7 | 5.5 | 5.6 | 5.6 | 6.2 | 6.6 | 6.2 | 6.0 | 6.3 |
| Average Lengthening (%) | | | 1.8 | | | | | 13.8 | | |

It will be appreciated that since the use of elastase or other enzymes to achieve the expansion of healthy skin was unknown prior to the present invention, there was no prior work available to guide the present inventor in determining the concentrations of enzyme and contact times required to effect the present invention. It will also be appreciated that the enzyme used in the above example was not of a pharmaceutical standard, and that the purer the enzyme used in accordance with the invention, the lower the concentration of the enzyme necessary to effect the invention.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A method for expanding healthy skin adjacent to an area which is to undergo reconstructive surgery, comprising administering to healthy skin adjacent to said area which is to undergo reconstructive surgery an efficacious amount of an enzyme which cleaves elastin fibers.

2. A method according to claim 1 wherein said enzyme is elastase or an elastase derivative.

3. A method according to claim 1 wherein said enzyme is administered by injection.

4. A method according to claim 1 wherein said enzyme is administered by topical application.

5. A method according to claim 1 wherein said enzyme is administered in an concentration selected from:

(a) a concentration of at least 1 unit of activity per $cm^2$ of skin; or (b) a concentration of at least 1 mg of enzyme per $cm^2$ of skin.

6. A method according to claim 1 wherein said healthy skin is adjacent to an area of skin which suffers from a condition or deficiency.

7. A method according to claim 6 wherein said condition or deficiency is selected from the group consisting of:

(a) skin loss after excision of a skin tumor or excision of necrotic skin;

(b) trauma;

(c) a congenital condition; and (d) a condition which has resulted or is likely to result in skin loss.

8. A method for increasing the surface area of a piece of skin to be applied as a skin graft, comprising contacting said piece of skin with an efficacious amount of an enzyme which cleaves elastin fibers.

9. A method according to claim 8 wherein said enzyme is elastase or an elastase derivative.

10. A method according to claim 8 wherein said piece of skin is contacted with said enzyme by injecting said enzyme into said piece of skin.

11. A method according to claim 8 wherein said piece of skin is contacted with said enzyme by topically applying said enzyme to said piece of skin.

12. A method according to claim 8 wherein said piece of skin is contacted with said enzyme by soaking said piece of skin in a solution containing said enzyme.

13. A method for increasing the yield of leather from an animal, comprising contacting the hide of said animal, or a portion of said hide, with an efficacious amount of an enzyme which cleaves elastin fibers while said hide or portion thereof is on said animal and said animal is alive.

14. A method according to claim 13 wherein said enzyme is elastase or an elastase derivative.

15. A method for increasing the yield of leather from an animal, comprising injecting into the hide of said animal, or a portion of said hide, an efficacious amount of an enzyme which cleaves elastin fibers.

16. A method according to claim 15 wherein said enzyme is elastase or an elastase derivative.

17. A method for expanding healthy skin adjacent to an area of skin loss, comprising administering to healthy skin which is adjacent to an area of skin loss an efficacious amount of an enzyme which cleaves elastin fibers.

18. A method according to claim 17 wherein said skin loss is due to one of the group consisting of:

(a) skin loss after excision of a skin tumor or excision of necrotic skin;

(b) a condition which has resulted or is likely to result in skin loss.

19. A method according to claim 18, wherein said skin loss is due to mastectomy, excision of a skin tumor or excision of necrotic skin.

20. A method according to claim 17, wherein said step of administering is done by injection.

21. A method according to claim 17 wherein said step of administering is done by topical application.

22. A method for improving the efficacy of reconstructive surgery of an area of skin suffering from a condition or deficiency, comprising administering to healthy skin which is adjacent to said area of skin suffering from a condition or deficiency an efficacious amount of an enzyme which cleaves elastin fibers and, after said step of administering, using the skin to which said enzyme has been administered to help cover the area of skin loss.

23. A method according to claim 22, wherein said condition or deficiency is selected from the group consisting of:

(a) skin loss after excision of a skin tumor or excision of necrotic skin;

(b) trauma;

(c) a congenital condition; and (d) a condition which has resulted or is likely to result in skin loss.

24. A method for decreasing the elastic resistance to pulling of healthy skin adjacent to an area of skin which is to undergo reconstructive surgery, comprising administering to healthy skin adjacent to an area of skin which is to undergo reconstructive surgery an efficacious amount of an enzyme which cleaves elastin fibers.

25. A method for decreasing the elastic resistance to pulling of healthy skin adjacent to an area of skin loss, comprising administering to healthy skin which is adjacent to an area of skin loss an efficacious amount of an enzyme which cleaves elastin fibers.

26. A method for decreasing the elastic resistance to pulling of a piece of skin to be applied as a skin graft, comprising contacting said piece of skin with an efficacious amount of an enzyme which cleaves elastin fibers.

* * * * *